United States Patent
Riemenschnitter

(10) Patent No.: US 7,872,167 B2
(45) Date of Patent: Jan. 18, 2011

(54) MOISTURE-ACTIVATABLE ADHESIVES FOR MEDICAL APPLICATION PURPOSES

(75) Inventor: Marc Riemenschnitter, Freiburg (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 286 days.

(21) Appl. No.: 10/532,999

(22) PCT Filed: Oct. 31, 2003

(86) PCT No.: PCT/EP03/12117

§ 371 (c)(1),
(2), (4) Date: Dec. 22, 2005

(87) PCT Pub. No.: WO2004/043504

PCT Pub. Date: May 27, 2004

(65) Prior Publication Data

US 2006/0149183 A1    Jul. 6, 2006

(30) Foreign Application Priority Data

Nov. 13, 2002    (DE) ................. 102 52 725

(51) Int. Cl.
*A61F 13/00*    (2006.01)
(52) U.S. Cl. ............ 602/52; 602/48; 424/448; 424/449
(58) Field of Classification Search ........... 602/52, 602/48; 424/443, 444, 448, 449; 604/304–308
See application file for complete search history.

(56) References Cited

U.S. PATENT DOCUMENTS

| 3,322,703 | A | * | 5/1967 | Lindemann ................. 524/21 |
| 4,505,976 | A |   | 3/1985 | Doehnert et al. |
| 6,375,963 | B1 | * | 4/2002 | Repka et al. ............... 424/402 |
| 6,682,721 | B2 | * | 1/2004 | Kim et al. ................... 424/53 |
| 2004/0068036 | A1 | * | 4/2004 | Halladay et al. .......... 524/439 |

FOREIGN PATENT DOCUMENTS

| DE | 40 01 714 | 7/1991 |
| DE | 19856101 | 6/2000 |
| EP | 0739626 | 10/1996 |
| WO | WO 9306144 A1 * | 4/1993 |
| WO | WO 0168045 | 9/2001 |
| WO | WO 02/087645 | 11/2002 |

OTHER PUBLICATIONS

Woolfson, A.D., et al., Development and Characterisation of a.

* cited by examiner

*Primary Examiner*—Kim M Lewis
(74) *Attorney, Agent, or Firm*—D. Peter Hochberg; Sean F. Mellino; Daniel J. Smola

(57) ABSTRACT

An adhesive for medical patches or for transdermal therapeutic systems which contains a component or a combination of at least two components, such as (a) polyvinyl alcohols, (b) cellulose derivatives, (c) polyethers, (d) acid anhydrides and their acids and salts, as well as (e) non-pressure-sensitive adhesive polyacrylates. The adhesive has a tackiness which is activated and/or increased by contact with moisture or by absorption of moisture.

8 Claims, No Drawings

MOISTURE-ACTIVATABLE ADHESIVES FOR MEDICAL APPLICATION PURPOSES

CROSS-REFERENCE TO RELATED APPLICATIONS

This application is a National Stage application of International Application No. PCT/EP03/012117, filed on Oct. 31, 2003, which claims priority of German application number 102 52 725.3, filed on Nov. 13, 2002.

BACKGROUND OF THE INVENTION

1. Field of the Invention

The present invention relates to moisture-activatable adhesives for medical application purposes. More particularly, the present invention relates to medical patches and transdermal therapeutic systems. The invention further comprises medical patches and transdermal therapeutic systems containing such moisture-activatable adhesives.

2. Description of the Prior Art

Medical patches and transdermal therapeutic systems (TTSs) generally possess a pressure-sensitive adhesive layer which enables self-adhesive attachment to the skin. In the case of transdermal therapeutic systems, the pressure-sensitive adhesive layer often also serves as an active substance reservoir, i.e. the pressure-sensitive adhesive contains one or more active substances which are delivered to the skin during the period of application.

In many cases, the pressure-sensitive adhesive layers of medical patches or of TTSs are made of polymers such as polyacrylates, polyisobutylenes, polyisoprenes or the like. A disadvantage of such pressure-sensitive adhesives, however, is that they adhere only poorly on a moist support. For this reason, when a patch or TTS is applied to a moist skin site the adhesion between the pressure-sensitive adhesive matrix layer of the patch or TTS and the skin may be insufficient. This problem exists in particular with patients who perspire vigorously, or with parts of the skin that show increased transpiration. Due to the insufficient adhesion, the patch or TTS may become detached entirely or partially so that the intended function can no longer be fulfilled. This may particularly affect the delivery of active substances from TTSs.

Because of the pressure-sensitive adhesive properties, that layer of a patch or TTS which is to be adhered to the skin has to be covered with a detachable protective film. Furthermore, some of the conventional pressure-sensitive adhesive compounds utilised for patches or TTSs have a strong tendency towards showing "cold flow", which may lead to the adhesive compound emerging from the patch or TTS during storage, and subsequently causing the patch or TTS to stick to its pack. In addition, the conventional pressure-sensitive adhesive compounds are disadvantageous in that they are prepared almost exclusively with organic solvents, which may lead to problems due to the residual solvent content.

Furthermore, with active substance-containing adhesive matrix layers, it must be taken into account that at least for some active substances or active substance types an excessively lipophile environment can have a negative effect on the release of the active substances from the matrix. As a consequence, it is no longer possible to achieve the intended active substance release rate.

SUMMARY OF THE INVENTION

An object of the present invention is to provide an adhesive for medical patches or TTSs which does not have the aforementioned disadvantages, and which possesses improved adhesive properties, in particular on a moist support.

This and other objects are achieved according to the description to follow and from the appended claims.

DETAILED DESCRIPTION OF THE INVENTION

According to the present invention, the adhesive for medical patches or transdermal therapeutic systems contains a component or a combination of at least two components from the group comprising (a) polyvinyl alcohols, (b) cellulose derivatives, (c) polyethers, (d) acid anhydrides and their acids and salts, as well as (e) non-pressure-sensitive adhesive polyacrylates.

It is of essential importance that the tackiness of the adhesives according to the invention is activated and/or increased by contact with moisture or by absorption of moisture. This particularly means that the adhesive layer produced from an adhesive according to the invention either (i) initially has no self-adhesive properties and only becomes tacky after being moistened or upon contact with a moist support (e.g. a moist skin site), or (ii) that an adhesive layer according to the invention is per se already pressure-sensitive adhesive but its adhesive effect is increased by absorption of moisture. In this manner, a reliable adhesive effect on moist or perspiring skin is ensured. In the context of the present invention, the term "moisture-activatable" means both that the tackiness may be initiated by the action of moisture, and that an existing pressure-sensitive adhesive property may be increased under the influence of moisture.

By utilizing the principle of moisture activatability it is possible to prepare adhesive layers which are non-adhesive or only slightly adhesive in dry condition (e.g. during storage), so that it is not necessary to cover this adhesive layer with a detachable protective film. Since the adhesive layers according to the invention are non-adhesive or only slightly adhesive in dry condition, they are not prone to "cold flow", which is a further advantage since the patches, TTSs etc. are thereby prevented from sticking to the package.

The property of the adhesive effect being activated or increased by absorption of moisture is essentially due to the formulation according to the invention of the composition of the adhesive, i.e. by a content of certain components or polymers according to the present invention. In this context it is additionally advantageous that in most cases hydrophile polymers, such as polyvinyl alcohols or cellulose derivatives, are used. A further advantage results from the fact that in many cases the adhesive masses can be prepared on the basis of water or using aqueous solvent mixtures, so that organic solvents can largely or totally be dispensed with. It is thereby possible to save complex examinations to determine the residual solvent content, possible skin irritating effects caused by solvents are avoided, and the costs for waste air disposal incurred in the production are reduced.

Finally, according to the invention, provision is also made for increasing the hydrophile character of the adhesives, and thereby of the layers of adhesive prepared therefrom, by adding further hydrophile polymers or hydrophile auxiliary substances. The adhesives according to the invention, and thereby the TTSs prepared therefrom, are therefore especially suitable for transdermal administration of active substances where a hydrophile environment, i.e. a hydrophile character of the active substance-containing adhesive matrix, has a positive effect on the release behaviour of the TTS.

The adhesive compositions according to one embodiment of the invention contain a combination of at least two components, selected from the group comprising (a) polyvinyl alcohols, (b) cellulose derivatives, (c) polyethers, (d) acid anhydrides and their acids and salts, as well as (e) non-pressure-sensitive adhesive polyacrylates, at least two of these components being selected from different classes (a) to (e). Such a combination may, for example, contain a polyvinyl alcohol (a) and a polyether (c).

Components suitable for the inventive, moisture-activatable adhesive composition are cellulose derivatives (b), especially cellulose derivatives from the group comprising hydroxypropyl methyl cellulose, hydroxypropyl cellulose, sodium carboxymethyl cellulose, methyl cellulose, hydroxyethyl cellulose and hydroxypropyl ethyl cellulose.

In accordance with further embodiments of the present invention, the moisture-activatable adhesives contain one or more polymers from the class of the polyethers (c), such as from the class of the polyvinyl alkyl ethers. The alkyl groups are alkyl groups with 1 to 20 C atoms; suitable are straight-chain, branched-chain and cyclic alkyl residues, especially polyvinyl methyl ethers, polyvinyl ethyl ethers, polyvinyl isobutyl ethers and polyvinyl cyclohexyl ethers.

Furthermore, copolymers of the mentioned polyvinyl ethers with other monomers, especially copolymers with carboxylic acid anhydrides, may be used to advantage as well.

Acid anhydride group-containing polymers, such as maleic acid anhydride-containing copolymers, are used as acid anhydrides (component d), for example copolymers of methyl vinyl ether and maleic acid anhydride. Such copolymers are available under the name of GANTREZ (from ISP), for example; Gantrez AN types (anhydride) are used with preference.

Apart from the above, salts or the acid forms of the indicated acid anhydrides may also be used to advantage, such as Gantrez S types (acid forms of AN types, e.g. Gantrez S 97 BF, cf. Example 3), for example.

Furthermore, maleic acid anhydride and other carboxylic acid anhydrides are also suitable as acid anhydrides.

It has furthermore proved advantageous to add non-pressure-sensitive adhesive polyacrylates, especially film-forming polyacrylates, such as EUDRAGIT® 40 D (Röhm), to the inventive adhesives as the component (e); by adding such film-forming, non-pressure-sensitive adhesive polymers it is possible to increase the duration of adhesion, and the adhesive behaviour may be influenced favourably. Further suitable film-forming polyacrylates are in principle known to those skilled in the art.

The proportion of the non-pressure-sensitive adhesive polymers, relative to the sum of the polymer components of the adhesive compound, can be varied within a wide range in order to adjust the desired adhesive properties; thus, the polyacrylate portion in such a formulation may amount to 25-95%-wt., such as 50-80%-wt., for example.

According to a one embodiment of the present invention, the adhesive contains at least one film-forming polymer from the group of the polyacrylates and at least one polymethyl vinyl ether-polymaleic acid anhydride copolymer (cf. Example 2).

The invention furthermore comprises moisture-activatable adhesive compositions with a content of polyvinyl alcohol (a). According to one embodiment of the present invention, the adhesive formulation contains polyvinyl alcohol(s) and at least one polymethyl vinyl ether-polymaleic acid anhydride copolymer, the portion of polyvinyl alcohol being 1-80%-wt., such as 5-55%-wt., relative to the sum of these two polymer components.

The components (a) polyvinyl alcohols, (b) cellulose derivatives, (c) polyethers, (d) acid anhydrides and their acids and salts and (e) non-pressure-sensitive polyacrylates are per se moisture-activatable in correspondence with their respective type, i.e. they become tacky after being moistened, or they are not tacky per se. For example, the components (a) (polyvinyl alcohols) and (b) (cellulose derivatives) are, according to their type, moisture-activatable and tacky per se, and their degree of tackiness may vary depending on the type.

This correspondingly applies to a copolymer of polyether (component (c)) and acid anhydride (component (d)), such as Gantrez AN-139 BF, as well as to acid-type Gantrez S-97 BF.

Where the adhesive contains a component (selected from components (a) to (e)) that is not per se tacky or moisture-activatable, this adhesive should additionally contain a portion of at least 5.0%-wt., or even at least 10.0% -wt., of a tacky, moisture-activatable component (selected from the components (a) to (e)).

If, for example, an adhesive according to the invention contains a combination of polyvinyl alcohol (component (a)) with a copolymer of polyether (component (c)) and acid anhydride (component (d)), and a type of polyvinyl alcohol is used that possesses practically no moisture-activatability as adhesive (e.g. MOWIOL® 28-99; cf. Example 1), the portion of the copolymer (sum of the components (c) and (d)) should amount to 5.0%-wt.

If, for example a combination of a copolymer of polyether (component (c)) and acid anhydride (component (d)), e.g. Gantrez AN 169 BF, with non-pressure-sensitive adhesive polyacrylates (component (e); e.g. EUDRAGIT® 4 NE 40 D) is used for an adhesive according to the invention, the portion of the copolymer (sum of the components (c) and (d)) should contain at least 10.0%-wt.

It may furthermore prove advantageous for adjusting the desired adhesive properties to admix further polymer components to the moisture-activatable adhesives according to the invention, such as polymers from the group comprising polyvinyl pyrrolidones, gelatine, starch and starch derivatives. Apart from that, a large number of further components is in principle suitable for the manufacture of the moisture-activatable adhesive substances, provided that they have properties that are similar to those of the polymers mentioned herein.

The invention furthermore provides that auxiliary substances or additives are added to the adhesive compositions, respectively the adhesive layers. Suitable for this purpose are in particular fillers (e.g. $SiO_2$), colourants (e.g. $TiO_2$), thickeners or viscosity-enhancing additives (e.g. aerosil), emulsifiers (e.g. polyethoxylated sorbitan fatty acid esters such as TWEEN® or polyethoxylated fatty alcohols such as BRIJ®), plasticizers (e.g. polyethylene glycol, glycerol), sweeteners (e.g. sorbitol, aspartame, saccharin), flavourings, preservatives (e.g. sorbic acid and its salts) and dehydrating agents (e.g. sodium sulfate).

Organic acids, particularly from the groups of the saturated alkanoic monocarboxylic acids, the saturated alkanoic dicarboxylic acids, and the hydroxyalkanoic acids (e.g. tartaric acid), are used as further additives. The number of C atoms in these carboxylic acids is may be within the range of 2 to 20. The addition of organic acids, such as carboxylic acids, leads to an increase in wet adhesion and to a prolongation of the duration of adhesion, brought about by interactions between acids and cellulose derivatives, especially sodium carboxymethyl cellulose, e.g. by partial esterification.

The total portion of polymers in the adhesives according to the invention, or in the adhesive layers produced therefrom, amounts to 45-99%-wt., relative to the adhesive compound or the adhesive layer; the remainder consists of auxiliary substance(s) or additive(s) and/or active substance(s), as well as optionally a solvent portion. Suitable as solvents for the inventive adhesive compositions are water, aqueous solvent mixtures, alcohols, esters (such as ethyl acetate, for example) and other polar solvents.

Particularly advantageous are in addition those adhesive formulations according to the invention which in addition to the moisture-activatable adhesive formulation contain one or more pressure-sensitive adhesive polymers. Such adhesives and the adhesive layers obtained therefrom thereby possess both the advantages of conventional pressure-sensitive adhesives and the advantages which are brought about by the moisture-activatable adhesive compositions according to the invention. The inventive adhesives which additionally contain pressure-sensitive adhesive polymers particularly stand out by the fact that their adhesive power is activated and/or even increased upon action of moisture. At the same time they also possess sufficient adhesive power when no skin moisture is present.

The pressure-sensitive adhesive polymers selected may be those from the group of the polyacrylates, polyisobutylenes and polyisoprenes, silicon adhesives and hot melt pressure-sensitive adhesives. Polyacrylates are understood to be polymers based on acrylic acid or methacrylic acid and their esters, as well as mixtures of such polymers. Suitable polyacrylates are known to the skilled artisan (cf. Example 3).

The portion of moisture-activatable or non-pressure-sensitive adhesive components (components (a) to (e)) here may be 40 to 60%-wt.

The moisture-activatable adhesive formulations according to the invention can be used to advantage to produce medical patches or transdermal therapeutic systems (TTSs). Such patches and systems comprise at least one moisture-activatable adhesive matrix layer made of an adhesive according to the invention or containing such adhesive; mixtures of such adhesives may likewise be used. The structure of such patches or TTSs is in principle known to those skilled in the art; apart from the mentioned adhesive layer(s), it comprises a carrier or backing layer (e.g. a plastics film such as PET film, or a textile material) to which the adhesive layer is applied. That side of the adhesive layer which adheres to the skin is usually covered with an adhesively coated protective film; this can, however, also be dispensed with, as mentioned hereinabove.

In principle, the moisture-activatable systems according to the invention can be used in all cases where a flat-shaped object has to be attached to a support, especially a moist support, for a certain period of time.

In the case of TTSs, the matrix layer, made of one (or more) moisture-activatable pressure-sensitive adhesive formulation(s) according to the invention, contains at least one active substance. This active substance may be present in the matrix layer in dissolved or dispersed form, in the form of an emulsion or in solid form. Active substances are understood to be, in principle, any substances, substance mixtures or preparations which are suitable for topical or transdermal administration and which can have a physiological effect in the human or animal body, especially medicinal active substances, hormones, trace elements, enzymes and antigens. The active substances may serve to carry out therapeutic, prophylactic or cosmetic treatment.

Particularly, the following active substances and active substance groups are suitable:

1. Salts of basic or acidic active substances from the group of the ACE inhibitors, anabolics, antidiabetics, antihypertonics, anti-infectives, anticoagulants, antirheumatics, diuretics, hormones, immunosuppressants, laxatives, lipid-lowering agents, CNS-active compounds, anti-epileptics, antihypertonics, coronary therapeutic agents, etc.;
2. substances whose activity is increased by admission of water, which leads to higher active substance flux rates;
3. hydrophile active substances which are hardly soluble in hydrophobic polymers, e.g. insulin, erythropoietin, growth factors, gonadoliberins, oxytocin, prolactin, calcitonin, parathyrin (parathormone), somatomedin, melanotropin.

According to an additional embodiment of the present invention, the moisture-activatable adhesive matrix of a medical patch, but particularly of a TTS, is connected with an overlying patch. The area of the latter is larger than that of the moisture-activatable adhesive matrix; namely, the overlying patch projects beyond the surface of the matrix layer at all sides thereof. It is furthermore advantageous to also provide the overlying patch with a pressure-sensitive adhesive polymer layer on the skin-facing side.

In the following, the invention will be illustrated by means of examples of formulations.

EXAMPLE 1

Moisture-activatable adhesive without addition of pressure-sensitive adhesive

| Component | Constituent amount |
|---|---|
| MOWIOL ® 28-99 | 9.1%-wt. |
| Gantrez AN-139 | 90.9%-wt. |
| Water | |

MOWIOL® 28-99: polyvinyl alcohol (by Hoechst/Aventis)

Gantrez AN-139: polymethyl vinyl ether-polymaleic acid anhydride copolymer (by ISP)

Process of manufacture: Demineralised water is placed in a suitable mixing vessel, and MOWIOL® 29-99 (polyvinyl alcohol) is introduced while stirring and dissolved completely at 80 to 90° C. Gantrez AN-139 (polymethyl vinyl ether polymaleic acid anhydride copolymer) is strewn into the solution, and this is likewise stirred under the influence of temperature (80-90° C.), until a homogenous mass is obtained.

EXAMPLE 2

Moisture-activatable adhesive with film-forming polyacrylate

| Component | Constituent amount |
|---|---|
| EUDRAGIT ® NE 40 D | 71.0%-wt. |
| Gantrez AN-169 | 28.6%-wt. |
| Sorbitol | 0.4%-wt. |
| Ethanol | |

EUDRAGIT® NE 40 D: non-pressure-sensitive adhesive, film-forming polyacrylate (by Röhm)

Gantrez AN-169: see Example 1.

Preparation: Ethanol is placed in a suitable mixing vessel, and sorbitol is strewn in while stirring and homogenising. EUDRAGIT® NE 40 D and Gantrez AN-169 are introduced while stirring, the mixture is stirred at approx. 50-70° C. until a homogenous mass is obtained.

EXAMPLE 3

Moisture-activatable adhesive with addition of pressure-sensitive adhesive

| Component | Constituent amount |
|---|---|
| Gantrez S-97 BF | 50.0%-wt. |
| DURO-TAK ® 326-2353 | 50.0%-wt. |
| Hexane | |
| Ethyl acetate | |
| Ethanol | |

DURO-TAK®326-2353: Polyacrylate pressure-sensitive adhesive (by National Starch & Chemical B.V.)

Gantrez S-97 BF: Acid form of a Gantrez AN polymer.

Manufacturing process: Ethanol is placed into a suitable mixing vessel, and Gantrez S-97 BF is introduced while stirring. This is stirred until a homogenous mass is obtained. Thereafter, the DURO-TAK® adhesive compound is stirred in.

The compounds prepared according to the above examples are coated, employing an Erichsen doctor knife, a spread coating box or a coating mechanism, on a suitable processing film and subsequently dried in the drying cabinet or the drying tunnel.

The adhesive films prepared according to Examples 1 and 2 are not self-adhesive, rather their tackiness is activated only by moistening the area provided for adhering or after moistening the polymer matrix, as well as upon contact with a moist substrate. The adhesive films produced according to Example 3 are already adhesive in dry state due to the addition of pressure-sensitive adhesive (DURO-TAK®). In preliminary tests, periods of adhesion to the skin in the range of 12 to 24 h were achieved with the exemplary formulations 1 and 2. After removing the active substance patches, which contained an adhesive film according to the above examples, from the skin no residues remained on the skin, or alternatively the residues could easily be washed off with water.

By means of the modifications described in the subclaims, it is possible to further optimize the adhesive effect.

What has been described above are preferred aspects of the present invention. It is of course not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, combinations, modifications, and variations that fall within the spirit and scope of the appended claims.

The invention claimed is:

1. An adhesive composition for preparing an adhesive layer for medical patches or for transdermal therapeutic systems, said adhesive layer having a tackiness which is activated and/or increased by contact with moisture or by absorption of moisture, wherein said adhesive layer comprises at least one pressure-sensitive adhesive polymer and at least one component selected from the group consisting of polyethers and acid anhydrides including acids and salts of acid anhydrides, said composition comprising:

polyvinylalcohol and at least one polymethyl vinyl ether-polymaleic acid anhydride copolymer, wherein the portion of polyvinylalcohol is 1-80%-wt, relative to the sum of said two polymers;

at least one film-forming polymer being at least one selected from the group consisting of non-pressure-sensitive adhesive polyacrylates and at least one pressure-sensitive adhesive polymer; and a solvent portion including a solvent.

2. The adhesive composition according to claim 1, wherein the solvent of said solvent portion is a polar solvent.

3. The adhesive composition according to claim 1, wherein the solvent of said solvent portion is selected from the group consisting of water, aqueous solvent mixtures, alcohols and esters.

4. The adhesive composition according to claim 1, wherein the solvent of said solvent portion comprises hexane and ethyl acetate.

5. The adhesive composition according to claim 1, wherein said at least one pressure-sensitive adhesive polymer is selected from the group consisting of polyacrylates, polyisobutylenes, polyisoprenes and silicone adhesives.

6. The adhesive composition according to claim 1, wherein said composition further comprises at least one component selected from the group consisting of cellulose derivatives and polyethers.

7. The adhesive composition according to claim 6, wherein said at least one cellulose derivative is selected from the group consisting of hydroxypropyl methyl cellulose, hydroxypropyl cellulose, sodium carboxymethyl cellulose, methyl cellulose, hydroxyethyl cellulose and hydroxypropyl ethyl cellulose.

8. The adhesive composition according to claim 6, wherein said polyethers are polyvinylalkyl ethers selected from the group consisting of polyvinyl methyl ether, polyvinyl ethyl ether, polyvinyl isobutyl ether and polyvinyl cyclohexyl ether.

* * * * *